(12) United States Patent
Nitta

(10) Patent No.: US 12,297,227 B2
(45) Date of Patent: May 13, 2025

(54) METHOD FOR EXTRACTING TARGET PROTEIN FROM BIOLOGICAL SAMPLE AND METHOD FOR ANALYZING TARGET PROTEIN

(71) Applicant: Mediford Corporation, Tokyo (JP)

(72) Inventor: Shin-ichiro Nitta, Tokyo (JP)

(73) Assignee: Mediford Corporation, Tokyo (JP)

( * ) Notice: Subject to any disclaimer, the term of this patent is extended or adjusted under 35 U.S.C. 154(b) by 754 days.

(21) Appl. No.: 16/618,787

(22) PCT Filed: Jun. 1, 2018

(86) PCT No.: PCT/JP2018/021292
§ 371 (c)(1),
(2) Date: Dec. 2, 2019

(87) PCT Pub. No.: WO2018/221745
PCT Pub. Date: Dec. 6, 2018

(65) Prior Publication Data
US 2020/0140482 A1    May 7, 2020

(30) Foreign Application Priority Data
Jun. 2, 2017   (JP) ................. 2017-110247

(51) Int. Cl.
*C07K 1/14*     (2006.01)
*G01N 1/40*     (2006.01)
*G01N 21/64*    (2006.01)

(52) U.S. Cl.
CPC ........... *C07K 1/145* (2013.01); *G01N 1/4044* (2013.01); *G01N 21/64* (2013.01)

(58) Field of Classification Search
None
See application file for complete search history.

(56) References Cited

U.S. PATENT DOCUMENTS

| | | |
|---|---|---|
| 6,849,714 B1 | 2/2005 | Bridon et al. |
| 2009/0176252 A1 | 7/2009 | Kojima et al. |
| 2011/0177601 A1 | 7/2011 | Kodera et al. |
| 2014/0199711 A1 | 7/2014 | Sakai et al. |

FOREIGN PATENT DOCUMENTS

| | | |
|---|---|---|
| JP | 2003-508350 A | 3/2003 |
| JP | 2007-10418 A | 1/2007 |
| JP | 2014-238338 A | 12/2014 |
| WO | WO 2009/019889 A1 | 2/2009 |
| WO | WO 2013/027823 A1 | 2/2013 |

OTHER PUBLICATIONS

Zhang et al., "Differential recovery of membrane proteins after extraction by aqueous methanol and trifluoroethanol", Proteomics 7: 1654-1663 (Year: 2007).*
Colantonio et al., "Effective removal of albumin from serum", Proteomics 5: 3831-3835 (Year: 2005).*
Crowell et al., "Maximizing recovery of water-soluble proteins through acetone precipitation", Analytica Chimica Acta 796: 48-54 (Year: 2013).*
Green and Hughes, "Protein fractionation on the basis of solubility in aqueous solutions of salts and organic solvents", Methods in Enzymology 1: 67-90 (Year: 1955).*
Dong et al., "Extraction and purification of IgG by hydrophilic organic solvent salting-out extraction", Journal of Chromatography B, 1012-1013 pp. 137-143 (Year: 2016).*
Thongbooknerd, V. et al., "Proteomic analysis of normal human urinary proteins isolated by acetone precipitation or ultracentrifugation", Kidney International vol. 62, pp. 1461-1469 (Year: 2002).*
Office Action issued in corresponding Japanese Application No. 2019-521356, issued on Jul. 13, 2021.
Tirumalai et al., "Molecular & Cellular Proteomics", vol. 2, No. 10, pp. 1096-1103 and Supplementary Material (2003).
Jensen, L., et al., Absorption, Metabolism and Excretion of the GLP-1 Analogue Semaglutide in Humans and Nonclinical Species, European Journal of Pharmaceutical Sciences 104:31-41, 2017.
Hall, T.G., et al., Identifying and Overcoming Matrix Effects in Drug Discovery and Development, Tandem Mass Spectrometry—Applications and Principles, J.K. Prasain, Ed., Chapter 18, pp. 389-420, Feb. 2012.
McCord, J.M., et al., Superoxide Dismutase, The Journal of Biological Chemistry 244(22):6049-6055, 1969.
Green, A.A., Studies in the Physical Chemistry of the Proteins, Journal of Biological Chemistry 95:47-66, 1932.
Cromwell, M.E.M., et al., Protein Aggregation and Bioprocessing, The AAPS Journal 8(3):E572-E579, 2006.
Mahler, H.-C., et al., Protein Aggregation: Pathways, Induction Factors and Analysis, Journal of Pharmaceutical Sciences 98(9):2909-2934, 2009.
Tirumalai, R.S., et al., Characterization of the Low Molecular Weight Human Serum Proteome, Molecular & Cellular Proteomics 2(10):1096-1103, 2003.
International Search Report received in PCT/JP2018/021292 dated Aug. 28, 2018.

\* cited by examiner

*Primary Examiner* — Anand U Desai
(74) *Attorney, Agent, or Firm* — Knobbe, Martens, Olson & Bear, LLP

(57) ABSTRACT

An object of the present invention is to provide a method of efficiently extracting a target protein contained in a biological sample such as serum or plasma, thereby enabling highly precise analysis. In the present invention, there is provided the method in which a protein is removed from a sample derived from a living body to extract the target protein, and a salt and/or urea at a high concentration, and a water-soluble organic solvent are used.

10 Claims, 1 Drawing Sheet
Specification includes a Sequence Listing.

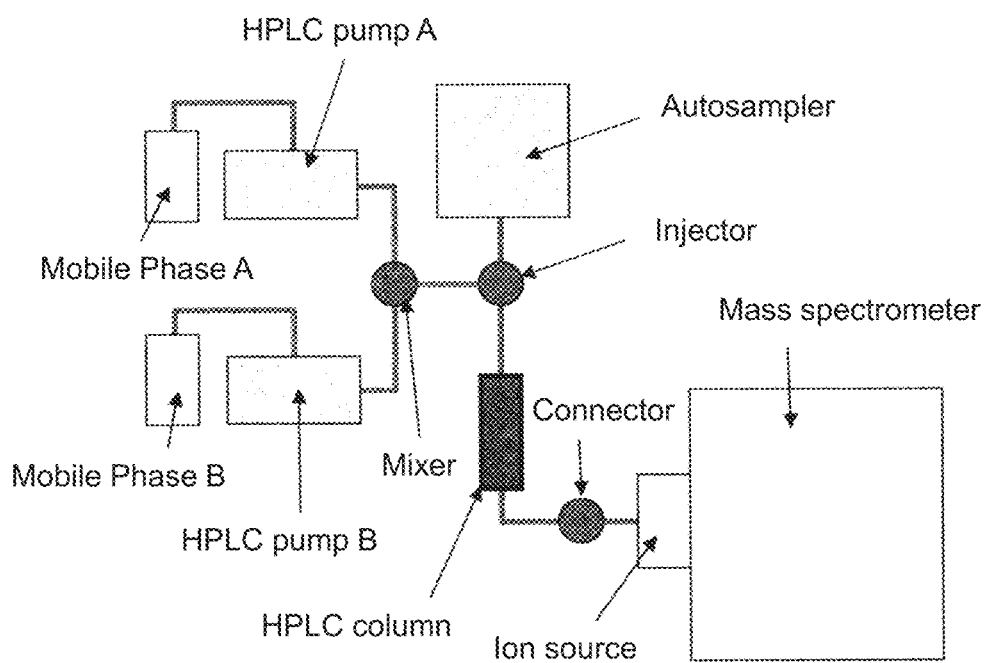

```
SEQUENCE LISTING

<160> NUMBER OF SEQ ID NOS: 5

<210> SEQ ID NO 1
<211> LENGTH: 37
<212> TYPE: PRT
<213> ORGANISM: Artificial Sequence
<220> FEATURE:
<223> OTHER INFORMATION: Synthetic GLP-1 peptide

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 30
<212> TYPE: PRT
<213> ORGANISM: Artificial Sequence
<220> FEATURE:
<223> OTHER INFORMATION: Synthetic GLP-1 peptide

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic GLP-1 peptide
<220> FEATURE:
<221> NAME/KEY: MISC_FEATURE
<222> LOCATION: (30)..(30)
<223> OTHER INFORMATION: AMIDATION

<400> SEQUENCE: 3
```

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Synthetic GLP-1 peptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 26
<212> TYPE: PRT
<213> ORGANISM: Artificial Sequence
<220> FEATURE:
<223> OTHER INFORMATION: Synthetic GLP-1 peptide

<400> SEQUENCE: 5

Ala Asn Ser Ala Val Val Ser Trp Asp Val Leu Glu Asp Glu Val Val
1               5                   10                  15

Ile Gly Phe Ala Ile Ser Gln Gln Lys Lys
            20                  25
```

METHOD FOR EXTRACTING TARGET PROTEIN FROM BIOLOGICAL SAMPLE AND METHOD FOR ANALYZING TARGET PROTEIN

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 2019-12-02_SEQ-TOYA228004APC, the date of creation of the ASCII text file is Dec. 2, 2019, and the size of the ASCII text file is 3 KB.

TECHNICAL FIELD

The present invention relates to: a method of efficiently extracting a target protein in the case of analyzing a target protein in a biological sample; a method of analyzing a target protein; and a pretreatment kit for deproteinization.

BACKGROUND ART

In recent years, analysis of trace substances contained in biological samples has increased in importance. In particular, analysis of biomarker proteins of which changes such as induction and reduction occur depending on diseases is more likely to be able to be utilized not only for diagnostic markers but also for targets for drug discovery, and therefore, development of measurement methods with high precision has received attention.

Methods such as ELISA assay and latex agglutination assay using antigen-antibody reaction have been conventionally used in analysis of proteins. However, such methods require production of respective antibodies corresponding to target proteins. In addition, measurement results very often depend on the reactivity of the antibodies, and thus have unreliable stability. In addition, measurement steps called manual measurement have demerits in view of troublesomeness and reproducibility.

However, measurement technologies based on high performance liquid chromatography and mass spectrometry have advanced, and such instrumental analyses have become commonplace not only for the purpose of research but also for use in clinical examination. The instrumental analyses have been considered to be able to be potent tools not only for measuring trace proteins but also for enabling the high-speed handling of a large amount of specimens, and measurement methods and instruments have been rapidly improved; however, the instrumental analyses have not yet been in positions to be able to be easily and quickly performed in clinical sites. Examples of the reasons thereof include insufficient establishment of extraction methods with high general applicability for high-speed treatment of a large amount of specimens with maintained measurement precision in actual sites for clinical examination because of setting of highly specific conditions for measurement of target substances in the measurement methods themselves.

Even if any type of analysis method is used, high-precision analysis of a minute amount of a target protein contained in a sample requires use in the analysis in a state in which contaminants other than the target protein, particularly contaminating protein components, of which tens of thousands of kinds or more are estimated to exist, are removed to enhance the recovery rate of the target protein, rather than use of a specimen such as plasma or serum without being processed. Examples of such contaminating proteins as described above include proteins with relatively high molecular weights, which can inhibit accurate measurement, such as albumin, globulin, and various proteases. Removal of such components has been demanded. The solution of such a point can be expected to result in drastic improvement in the swiftness of diagnosis of clinical examination.

Examples of methods of removing such contaminating proteins (hereinafter, may be simply referred to as "deproteinization") include a method in which insolubilization caused by protein denaturation is utilized, a method with physical removal, and a method in which a protein is directly injected into LC (liquid chromatography) to on-line remove the protein.

The method in which insolubilization caused by protein denaturation is utilized is a method in which the higher-order structure of a protein is broken to denature and precipitate the protein. Specific examples thereof include a method in which an acid (perchloric acid, trichloroacetic acid, or metaphosphoric acid) or an organic solvent (acetone, acetonitrile, methanol, or ethanol) is added, and a method in which heating and cooling are performed. Such a method is widely used because a protein having a relatively high molecular weight can be easily removed; however the method has demerits that the method is often ineffective for various target proteins, unexpected chemical reaction may occur, and it is necessary to confirm in advance that the concentration of a substance of interest is not influenced.

The method with physical removal is a method that utilizes ultrafiltration (a membrane filter, a centrifugal filtration device, or the like), dialysis (a dialysis tube), ultracentrifugation, or the like, and separates a target protein of interest with the utilization of a difference in molecular size. Because of mild conditions, the method has a merit that there is little fear of a side reaction, and a centrifugation-type product can allow ultrafiltration operation to be performed by simple operation. However, it is necessary to select a membrane having a molecular cutoff according to a purpose in view of the nonspecific adsorption of a substance of interest and the capability of the membrane to allow fluid to permeate the membrane. Because the selection of a membrane and the conditions of centrifugation are influenced by the properties, concentration, pH conditions of a sample, and the like, confirmation in a preliminary experiment is required, and considerable effort is required for obtaining general-purpose properties.

The method in which a sample containing a target protein is directly injected into LC to perform on-line deproteinization uses a restricted-access filler column (an internal surface reversed-phase filler, a hybrid filler, or a hydrophilic polymer filler) having the function of eluting a high-molecular substance such as serum protein by size exclusion without denaturation of the high-molecular substance and holding a low-molecular substance such as a drug by hydrophobic interaction or electrostatic interaction. A column switching method is often performed in which deproteinization is performed with a restricted-access filler column to analyze a component of interest with another column. This method has a feature that a sample can be injected into LC only by passing the sample through a filter of around 0.2 μm. However, an effort is required for setting general-purpose conditions because the columns are used in combination. In addition, the sample is directly injected, and therefore, the columns are considerably degraded, whereby the necessity of frequently switching the columns may be caused.

In addition to the methods described above, methods such as a fractionation method using an organic solvent, and ammonium sulfate precipitation with the utilization of the effect of salting out (coagulation) have been particularly used for a long time as methods of purifying a protein. However, these methods require a step of redissolving a protein which has been once precipitated.

For example, in the case of performing deproteinization by adding an organic solvent to serum and plasma, there has been a problem that a recovery rate is considerably decreased, such as occurrence of a phenomenon that a high-molecular weight protein to be removed and a target protein of interest coprecipitate. Moreover, it has been known that improvement in recovery rate may be expected in a case in which deproteinization is performed by adding a surfactant before adding an organic solvent. However, a case in which a subsequently used analysis method is an HPLC method is prone to result in the degradation of a column, and a case in which the subsequently used analysis method is mass spectrometry results in ionization suppression due to use of the surfactant and in desensitization due to the contamination of an ion source. Even in the case of the ELISA assay or the like in which no instrument is used, a surfactant affects immune reaction, and it is often impossible to obtain an expected result.

In the case of selecting analysis in which a high performance liquid chromatograph or a mass spectrometer is used as an analytical instrument, compatibility between a solvent used in pretreatment and a solvent used in instrumental analysis, ionization suppression, and the like must be taken into consideration, and it has been impossible to achieve simple analysis with high general-purpose properties and sufficiently highly precise performance in such pretreatment methods described above.

PRIOR ART DOCUMENTS

Non Patent Literature

[Non Patent Literature 1] Jensen et al. Eur. J. Pharm. Sci. 104; 31-41, 2017

[Non Patent Literature 2] Prasain et al. Tandem Mass Spectrometry-Applications and Principles Chap. 18, pp 390-420

[Non Patent Literature 3] McCord et al. J Biol. Chem. 244(22); 6049-55, 1969

[Non Patent Literature 4] Green et al. J. Biol. Chem. 95; 47, 1932

[Non Patent Literature 5] Cromwell M E et al. AAPS J. 8(3); E572-9, 2006

[Non Patent Literature 6] Mahler H C et al. J Pharm Sci. 98(9); 2909-34, 2009

SUMMARY OF INVENTION

Technical Problem

As described above, a method in which a target protein contained in a biological sample can be efficiently extracted has been demanded. An object of the present invention is to provide a method of efficiently extracting a target protein contained in a biological sample such as serum or plasma, thereby enabling highly precise analysis.

In the present invention, analysis is intended to include not only measurement steps such as detection and quantification of a target protein but also analyses obtained from measurement results therefrom.

Solution to Problem

As a result of intensive examination for solving such problems described above, the present inventors found that addition of a salt and/or urea at a high concentration to a biological sample enables a target protein to be extracted at a high recovery rate. The present invention accomplished a method of extracting a target protein from a biological sample, and a pretreatment kit, for performing measurement with precision and high sensitivity, on the basis of such findings.

In other words, the present invention provides the following.

[1] A method of extracting a target protein from a sample derived from a living body by a deproteinization method, wherein a salt and/or urea at a high concentration, and a water-soluble organic solvent are used.

[2] The method according to [1], wherein the water-soluble organic solvent is one or more selected from methanol, ethanol, isopropanol, acetone, and acetonitrile.

[3] The method according to any one of [1] or [2], wherein the salt is an ammonium salt, a sodium salt, a potassium salt, or a magnesium salt.

[4] The method according to any one of [1] to [3], wherein the salt is one or more salts selected from ammonium formate, ammonium carbonate, ammonium hydrogen carbonate, ammonium acetate, urea, ammonium dihydrogen phosphate, diammonium hydrogen phosphate, sodium dihydrogen phosphate, disodium hydrogen phosphate, potassium dihydrogen phosphate, dipotassium hydrogen phosphate, sodium dihydrogen pyrophosphate, sodium pyrophosphate, potassium pyrophosphate, sodium chloride, potassium chloride, magnesium chloride, ammonium sulfate, sodium sulfate, sodium acetate, sodium hydrogen carbonate, and sodium carbonate.

[5] The method according to any one of [1] to [4], wherein the salt and/or urea at a concentration of 0.02 to 8 M is added into a sample, followed by removing a protein.

[6] The method according to any one of [1] to [5], wherein an amount of added water-soluble organic solvent is twice or more (v/v) an amount of a sample derived from a living body.

[7] The method according to any one of [1] to [6], wherein the target protein is a protein that can be dissolved in a water-soluble organic solvent.

[8] The method according to any one of [1] to [7], wherein the target protein has a molecular weight of 50,000 or less.

[9] The method according to any one of [1] to [8], wherein the target protein is one or more selected from a group consisting of glucagon or an analog thereof, glucagon-like peptide-1 (GLP-1) or an analog thereof, glucose-dependent insulinotropic polypeptide (GIP) or an analog thereof, an incretin other than the above or an analog thereof, partial peptides (for example, K1 to K20) of keratin (cytokeratin) or analogs thereof, dynorphin or an analog thereof, GRF or an analog thereof, insulin or an analog thereof, an HIV virus-derived peptide (for example, T-20, T-1249, or C-34) or an analog thereof, an SR protein family (for example, SF2, ASF, SC35, SRp40, SRp55, or the like) or an analog thereof, peptide YY (PYY) or an analog thereof, adrenocorticotrophic hormone (ACTH) or an analog thereof, corticotropin-releasing hormone (CRH) or an analog thereof, corticotropin-like intermediate-lobe peptide (CLIP) or an analog thereof, melanocyte-stimulating hormone (MSH) or an analog thereof, lipotropin (LPH) or an analog thereof, amyloid β (Aβ) or an analog thereof, growth hormone (GH) or an analog thereof, a growth hormone-releasing factor (GRF or GHRF) or an analog thereof, various growth factors and growth stimulators such as insulin-like growth factor 1 (IGF-1) or insulin-like growth factor 2 (IGF-2), or analogs thereof, a VGF-derived peptide (TLPQ-21, TLPQ-62, AQEE-30, or LQEQ-19) or an analog thereof, isoleucyl-seryl-bradykinin or an analog thereof, a natriuretic peptide (ANP, BNP, or CNP) or an analog thereof, a natriuretic factor (ANF, BNF, or CNF) or an analog thereof, a precursor (for example, pre-proANP, proANP, NT-proANP, pre-proBNP, proBNP, NT-proBNP, pre-proCNP, proCNP, or NT-proCNP) of a natriuretic peptide, or an analog thereof, midkine (MK) or an analog thereof, a neuromedin (for example, neuromedin C, neuromedin B, neuromedin U, neuromedin S, neuromedin K, neuromedin N, or the like) or an analog thereof, gastrin or an analog thereof, gastrin-releasing peptide or an analog thereof, endorphin (EP) or an analog thereof, neoendorphin or an analog thereof, proopiomelanocortin (POMC) or an analog thereof, enkephalin (PENK) or an analog thereof, dynorphin or an analog thereof, adrenorphin or an analog thereof, amidorphin or an analog thereof, opiorphin or an analog thereof, casomorphin or an analog thereof, gluten exorphin or an analog thereof, gliadorphin or an analog thereof, rubiscolin or an analog thereof, deltorphin or an analog thereof, an opioid peptide such as dermorphin, or an analog thereof, adrenomedullin (AM) or an analog thereof, a neuropeptide such as neuropeptide 1, neuropeptide 2, neuropeptide AF, neuropeptide B, neuropeptide FF, neuropeptide G, neuropeptide K, neuropeptide S, neuropeptide SF, neuropeptide W, neuropeptide Y, neuropeptide Y C-terminal flanking peptide, neuropeptide γ, neuropeptide NEI, or neuropeptide NGE, or an analog thereof, nociceptin (orphanin FQ) or an analog thereof, an oxytocin (OT or OXT) or an analog thereof, urocortin or an analog thereof, interferon-γ or an analog thereof, rat neutrophil chemotactic factor-1 or an analog thereof (CINC-1/gro), parathyroid hormone or an analog thereof (PTH), ovalbumin or an analog thereof (OVA), angiotensinogen, angiotensins I to IV or analogs thereof, irisin or an analog thereof, substance P or an analog thereof, neurokinin A or an analog thereof, neurokinin B or an analog thereof, copeptin or an analog thereof, ghrelin or an analog thereof, motilin or an analog thereof, erythropoietin or an analog thereof, endothelin or an analog thereof, luteinizing hormone or an analog thereof, orexin or an analog thereof, pituitary adenylate cyclase-activating peptide or an analog thereof, calcitonin or an analog thereof, calcitonin gene-related peptide or an analog thereof, katacalcin or an analog thereof, vasoactive intestinal peptide or an analog thereof, thyrotropin-releasing hormone (TRH) or an analog thereof, cholecystokinin or an analog thereof, plant peptide hormone or an analog thereof, gonadotrophic hormone or an analog thereof, secretin or an analog thereof, somatostatin or an analog thereof, pregnant mare serum gonadotropin or an analog thereof, vasopressin (VP) or an analog thereof, vasotocin or an analog thereof, parathormone (PTH) or an analog thereof, bombesin or an analog thereof, follicle-stimulating hormone or an analog thereof, leuprorelin or an analog thereof, relaxin or an analog thereof, liraglutide or an analog thereof, leptin or an analog thereof, peptide B or an analog thereof, peptide E or an analog thereof, peptide F or an analog thereof, BAMP22P or an analog thereof, morphine or an analog thereof, neurophysin 1 or an analog thereof, neurophysin 2 or an analog thereof, anthorine or an analog thereof, cortistatin or an analog thereof, RF amide-related peptide or an analog thereof, pancreatic polypeptide Y or an analog thereof, pancreatic polypeptide YY (PP) or an analog thereof, islet amyloid polypeptide or an analog thereof, amylin or an analog thereof, intermedin or an analog thereof, ranatensin or an analog thereof, glicentin or an analog thereof, oxyntomodulin or an analog thereof, vasoactive intestinal peptide (VIP) or an analog thereof, pituitary adenylate cyclase activating polypeptide (PACPA) or an analog thereof, somatoliberin or an analog thereof, somatorelin or an analog thereof, sermorelin or an analog thereof, urotensin or an analog thereof, kininogen or an analog thereof, kallidin or an analog thereof, kinin or an analog thereof, neurotensin or an analog thereof, chromogranin or an analog thereof, granin or an analog thereof, vasostatin or analogs thereof, secretogranin or an analog thereof, CCB or an analog thereof, GAWK or an analog thereof, EM66 or an analog thereof, obestatin or an analog thereof, galanin or an analog thereof, galanin message-associated peptide or an analog thereof, galanin-like peptide or an analog thereof, gonadotrophic hormone-releasing hormone (GnRH) or an analog thereof, gonadoliberin or an analog thereof, neurexophilins (NXPHs) 1 to 4 or analogs thereof, parathormone-like hormone (PTHLH) or an analog thereof, osteostatin or an analog thereof, melanin-concentrating hormone (MCH) or an analog thereof, hypocretin or an analog thereof, cocaine- and amphetamine-regulated transcript (CART) or an analog thereof, agouti-related peptide (AGRP) or an analog thereof, prolactin or an analog thereof, prolactin-releasing peptide (PrRP) or an analog thereof, apelin or an analog thereof, kisspeptin or an analog thereof, metastin or an analog thereof, diazepam binding inhibitor or an analog thereof, cerberin (CBLN) or an analog thereof, obesin or an analog thereof, adiponectin or an analog thereof, visfatin or an analog thereof, PBEF or an analog thereof, resistin or an analog thereof, an adipose tissue-specific secretory factor or an analog thereof, a hypoxia-induced mitogenic factor (HIMF, FIZZ, or RELM) or an analog thereof, colon/intestine-specific cysteine-rich protein or an analog thereof, colon cancer-specific gene product or an analog thereof, secretory DNA/calcium-binding protein nuclebindin or an analog thereof, or nesfatin or an analog thereof.

[10] The method according to any one of [1] to [9], wherein the sample is blood, plasma, or serum.

[11] The method according to any one of [1] to [10], comprising the following steps 1 to 4:

(step 1) the step of adding a salt and/or urea at a high concentration to a collected biological sample with stirring;

(step 2) the step of adding a water-soluble organic solvent to the sample to which the salt and/or urea at the high concentration have been added in the step 1;

(step 3) the step of separating the sample to which the water-soluble organic solvent has been added in the step 2; and (step 4) the step of collecting a supernatant after the separation in the step 3.

[12] A method of analyzing a target protein, comprising collecting a supernatant containing a target protein by the method according to [11], and analyzing the target protein using the supernatant.

[13] The method according to [12], wherein the target protein is analyzed by a UV detector, a fluorescence detector, or a mass spectrometer.

[14] A pretreatment kit for deproteinization, comprising a salt and/or urea in a state of being able to be mixed with a sample, and a water-soluble organic solvent.

[15] A pretreatment kit for deproteinization, comprising a salt and/or urea in a state of being able to be mixed with a sample, and a filter for deproteinization or a deproteinization column.

[16] The pretreatment kit for deproteinization according to [15], wherein a support included in the filter for deproteinization is at least one or more selected from polypropylene (PP), polyvinylidene fluoride (PVDF), glass fiber (GF), polyether sulfone (PES), nylon (NY), polytetrafluoroethylene (PTFE), regenerated cellulose (RC), cellulose acetate (CA), and methacrylate butadiene styrene (MBS).

[17] The pretreatment kit for deproteinization according to [15] or [16], comprising a water-soluble organic solvent.

[18] The pretreatment kit for deproteinization according to any one of [14] to [17], wherein the salt and/or the urea are contained to have a concentration of 0.02 to 8 mol/L.

[19] The pretreatment kit for deproteinization according to any one of [14] to [18], comprising at least one additive selected from a preservative, a stabilizer, and a buffer.

[20] A method of measuring a target protein, comprising pretreating a sample derived from a living body using the pretreatment kit for deproteinization according to any one of [14] to [19], and measuring a presence and/or amount of a target protein in the pretreated sample.

Advantageous Effects of Invention

Use of the extraction method of the present invention enables efficient extraction of a target protein contained in a biological sample such as serum or plasma, and enables highly precise analysis of the target protein.

BRIEF DESCRIPTION OF DRAWINGS

FIG. 1 is a conceptual diagram illustrating one aspect of an LC-MS system.

DETAILED DESCRIPTION OF THE PREFERRED EMBODIMENTS

Embodiments of the present invention will be described in detail below. However, aspects of a use method are not limited thereto.

The present invention relates to a method of extracting a target protein from a biological sample. In the method, a non-target protein is removed from a biological sample by using a salt and/or urea at a high concentration as well as a water-soluble organic solvent. Pretreatment herein is intended to include the meaning of extraction and recovery, and the extraction and the recovery may be used as substantially synonymous words.

In the present invention, a biological sample includes a component derived and collected from a living body, and examples thereof include whole blood, plasma, serum, urine, stool, saliva, sputum, sperm, a secretion, excreta, or swab from the vagina, the nose, the rectum, the urethra, or the pharynx, secretory fluid from the lacrimal duct, bronchoalveolar lavage fluid (BALF) such as brush washing liquid, pleural effusion, or a biopsy tissue sample. The biological sample may be applied to the method of the present invention without being processed, or a substance obtained by dissolving or suspending the biological sample in water, an acid, an alkali, an organic solvent, or a liquid mixture thereof, and by further performing treatment of the resultant as needed may be applied to the method of the present invention.

In the present invention, a component of a protein is not particularly limited to that derived from a membrane, cytoplasm or the like, and the protein can be intended to be a polymer compound formed by binding a number of amino acids in chain form. In addition to any proteins derived from living bodies, and any naturally occurring proteins to which a carbohydrate chain, a phosphate group, or the like is added, and which is modified, the protein may also be intended to be a sequence that does not exist in the natural world, a modification, or an adduct. A protein formed by binding a large number of amino acids in chain form is acceptable, and the protein may also be intended to be, for example, a peptide preparation or the like. In addition, a protein having amino acid sequences of which some are substituted, deleted, inserted, or added is also acceptable.

The number of amino acids included in a target protein to be analyzed is not particularly limited, and a protein that can be dissolved in a water-soluble organic solvent can be regarded as the target protein, as described later. Specifically, a protein having a molecular weight of 50,000 or less is preferred, a protein having a molecular weight of 25,000 or less is more preferred, a protein having a molecular weight of 12,000 or less is still more preferred, and a molecular weight of 8,000 or less is most preferred.

The target protein may be a protein having a specific function, or may be a part thereof. Moreover, a peptide is also acceptable. Such a peptide (hereinafter, may be referred to as "target polypeptide") encompasses all polypeptides of which the molecular weight, isoelectric point, function, structure, and the like are not limited, and such a target polypeptide encompasses all of known polypeptides or unknown polypeptides. Herein, "polypeptide" is a generic term including all of proteins, polypeptides, and oligopeptides, and the minimum size thereof is 2 amino acids. The target polypeptide is not limited to polypeptides derived from living bodies such as various tissues, cells, bacteria, and viruses but encompasses all of polypeptides synthesized by known synthesis methods, polypeptides obtained by known genetic engineering techniques, the polypeptide fragments of certain proteins formed by enzymatic digestion by various proteases, and polypeptides that can be purchased as standard samples.

Analogs available in the present invention may be analogs derived from a common precursor, and include, for example, all of plural kinds of existing partial peptides, homologs, paralogs, orthologs, analogs, and the like. The definitions of such terms have the same meanings as those of terms currently widely commonly used in the related fields of biology, biochemistry, physiology, molecular biology, biotechnology, and the like. A precursor itself can also be intended to be a target protein.

The target polypeptide may be a polypeptide included in a sample prepared by a known preparation method such as a known preparation method, for example, centrifugal treatment, denaturation treatment, fractionation treatment with ammonium sulfate or the like, dialysis treatment, or purification treatment with ultrafiltration, ion chromatography, or the like, as well as a polypeptide included in a sample derived from a living body, completely dissolved or suspended in water, an acid, an alkali, an organic solvent, or a liquid mixture thereof.

A target polypeptide included in a target polypeptide-containing sample may be one or more kinds. In other words, many kinds of polypeptides can be simultaneously detected or quantified using the present method. Such a peptide may be a peptide having the molecular weight described above. Examples thereof include, but are not limited to, glucagon or an analog thereof, glucagon-like peptide-1 (GLP-1) or an analog thereof, glucose-dependent insulinotropic polypeptide (GIP) or an analog thereof, an incretin other than the above or an analog thereof, partial peptides (for example, K1 to K20) of keratin (cytokeratin) or analogs thereof, dynorphin or an analog thereof, GRF or an analog thereof, insulin or an analog thereof, an HIV virus-derived peptide (for example, T-20, T-1249, or C-34) or an analog thereof, an SR protein family (for example, SF2, ASF, SC35, SRp40, SRp55, or the like) or an analog thereof, peptide YY (PYY) or an analog thereof, adrenocorticotrophic hormone (ACTH) or an analog thereof, corticotropin-releasing hormone (CRH) or an analog thereof, corticotropin-like intermediate-lobe peptide (CLIP) or an analog thereof, melanocyte-stimulating hormone (MSH) or an analog thereof, lipotropin (LPH) or an analog thereof, amyloid β (Aβ) or an analog thereof, growth hormone (GH) or an analog thereof, a growth hormone-releasing factor (GRF or GHRF) or an analog thereof, various growth factors and growth stimulators such as insulin-like growth factor 1 (IGF-1) or insulin-like growth factor 2 (IGF-2), or analogs thereof, a VGF-derived peptide (TLPQ-21, TLPQ-62, AQEE-30, or LQEQ-19) or an analog thereof, isoleucyl-seryl-bradykinin or an analog thereof, a natriuretic peptide (ANP, BNP, or CNP) or an analog thereof, a natriuretic factor (ANF, BNF, or CNF) or an analog thereof, a precursor (for example, pre-proANP, proANP, NT-proANP, pre-proBNP, proBNP, NT-proBNP, pre-proCNP, proCNP, or NT-proCNP) of a natriuretic peptide, or an analog thereof, midkine (MK) or an analog thereof, a neuromedin (for example, neuromedin C, neuromedin B, neuromedin U, neuromedin S, neuromedin K, neuromedin N, or the like) or an analog thereof, gastrin or an analog thereof, gastrin-releasing peptide or an analog thereof, endorphin (EP) or an analog thereof, neoendorphin or an analog thereof, proopiomelanocortin (POMC) or an analog thereof, enkephalin (PENK) or an analog thereof, dynorphin or an analog thereof, adrenorphin or an analog thereof, amidorphin or an analog thereof, opiorphin or an analog thereof, casomorphin or an analog thereof, gluten exorphin or an analog thereof, gliadorphin or an analog thereof, rubiscolin or an analog thereof, deltorphin or an analog thereof, an opioid peptide such as dermorphin, or an analog thereof, adrenomedullin (AM) or an analog thereof, a neuropeptide such as neuropeptide 1, neuropeptide 2, neuropeptide AF, neuropeptide B, neuropeptide FF, neuropeptide G, neuropeptide K, neuropeptide S, neuropeptide SF, neuropeptide W, neuropeptide Y, neuropeptide Y C-terminal flanking peptide, neuropeptide γ, neuropeptide NEI, or neuropeptide NGE, or an analog thereof, nociceptin (orphanin FQ) or an analog thereof, an oxytocin (OT or OXT) or an analog thereof, urocortin or an analog thereof, interferon-γ or an analog thereof, rat neutrophil chemotactic factor-1 or an analog thereof (CINC-1/gro), parathyroid hormone or an analog thereof (PTH), ovalbumin or an analog thereof (OVA), angiotensinogen, angiotensins I to IV or analogs thereof, irisin or an analog thereof, substance P or an analog thereof, neurokinin A or an analog thereof, neurokinin B or an analog thereof, copeptin or an analog thereof, ghrelin or an analog thereof, motilin or an analog thereof, erythropoietin or an analog thereof, endothelin or an analog thereof, luteinizing hormone or an analog thereof, orexin or an analog thereof, pituitary adenylate cyclase-activating peptide or an analog thereof, calcitonin or an analog thereof, calcitonin gene-related peptide or an analog thereof, katacalcin or an analog thereof, vasoactive intestinal peptide or an analog thereof, thyrotropin-releasing hormone (TRH) or an analog thereof, cholecystokinin or an analog thereof, plant peptide hormone or an analog thereof, gonadotrophic hormone or an analog thereof, secretin or an analog thereof, somatostatin or an analog thereof, pregnant mare serum gonadotropin or an analog thereof, vasopressin (VP) or an analog thereof, vasotocin or an analog thereof, parathormone (PTH) or an analog thereof, bombesin or an analog thereof, follicle-stimulating hormone or an analog thereof, leuprorelin or an analog thereof, relaxin or an analog thereof, liraglutide or an analog thereof, leptin or an analog thereof, peptide B or an analog thereof, peptide E or an analog thereof, peptide F or an analog thereof, BAMP22P or an analog thereof, morphine or an analog thereof, neurophysin 1 or an analog thereof, neurophysin 2 or an analog thereof, anthorine or an analog thereof, cortistatin or an analog thereof, RF amide-related peptide or an analog thereof, pancreatic polypeptide Y or an analog thereof, pancreatic polypeptide YY (PP) or an analog thereof, islet amyloid polypeptide or an analog thereof, amylin or an analog thereof, intermedin or an analog thereof, ranatensin or an analog thereof, glicentin or an analog thereof, oxyntomodulin or an analog thereof, vasoactive intestinal peptide (VIP) or an analog thereof, pituitary adenylate cyclase activating polypeptide (PACPA) or an analog thereof, somatoliberin or an analog thereof, somatorelin or an analog thereof, sermorelin or an analog thereof, urotensin or an analog thereof, kininogen or an analog thereof, kallidin or an analog thereof, kinin or an analog thereof, neurotensin or an analog thereof, chromogranin or an analog thereof, granin or an analog thereof, vasostatin or analogs thereof, secretogranin or an analog thereof, CCB or an analog thereof, GAWK or an analog thereof, EM66 or an analog thereof, obestatin or an analog thereof, galanin or an analog thereof, galanin message-associated peptide or an analog thereof, galanin-like peptide or an analog thereof, gonadotrophic hormone-releasing hormone (GnRH) or an analog thereof, gonadoliberin or an analog thereof, neurexophilins (NXPHs) 1 to 4 or analogs thereof, parathormone-like hormone (PTHLH) or an analog thereof, osteostatin or an analog thereof, melanin-concentrating hormone (MCH) or an analog thereof, hypocretin or an analog thereof, cocaine- and amphetamine-regulated transcript (CART) or an analog thereof, agouti-related peptide (AGRP) or an analog thereof, prolactin or an analog thereof, prolactin-releasing peptide (PrRP) or an analog thereof, apelin or an analog thereof, kisspeptin or an analog thereof, metastin or an analog thereof, diazepam binding inhibitor or an analog thereof, cerberin (CBLN) or an analog thereof, obesin or an analog thereof, adiponectin or an analog thereof, visfatin or an analog thereof, PBEF or an analog thereof, resistin or an analog thereof, an adipose tissue-specific secretory factor or an analog thereof, a hypoxia-induced mitogenic factor (HIMF, FIZZ, or RELM) or an analog thereof, colon/intestine-specific cysteine-rich protein or an analog thereof, colon cancer-specific gene product or an analog thereof, secretory DNA/calcium-binding protein nuclebindin or an analog thereof, or nesfatin or an analog thereof, or precursors of the peptides described above.

An extraction method that can be used in the present invention has a feature that a salt and/or urea at a high concentration, and an organic solvent are used, and can be performed according to, for example, the following steps:

(step 1) the step of adding a salt and/or urea at a high concentration to a collected biological sample with stirring;

(step 2) the step of adding a water-soluble organic solvent to the sample to which the salt and/or urea at the high concentration have been added in the step 1;

(step 3) the step of separating the sample to which the water-soluble organic solvent has been added in the step 2; and (step 4) the step of collecting a supernatant after the separation in the step 3.

An example of the extraction method that can be used in the present invention according to the steps described above will be described below; however, the present invention is not limited thereto.

A salt that can be used in the present invention may be solid or liquid. The salt is not particularly limited as long as being a nonvolatile salt solution, a volatile salt solution, a nonvolatile salt itself, or a volatile salt itself. As the salt, a salt solution having a relatively high polarity can be used. Use of a volatile salt solution or a volatile salt is preferred for, for example, analysis using a mass spectrometer as a detector. The salt solution is not particularly limited as long as being obtained by dissolving a salt in a liquid. As the salt solution, a solution obtained by dissolution in, for example, purified water or the like can be used. The salt solution can contain a buffer, and may be optimized in terms of a pH, the kind of a solvent, the kind of a salt, and a salt concentration.

Examples of the kind of the salt include ammonium salts, sodium salts, potassium salts, and magnesium salts. More specific examples thereof include ammonium formate, ammonium carbonate, ammonium hydrogen carbonate, ammonium acetate, urea, ammonium dihydrogen phosphate, diammonium hydrogen phosphate, sodium dihydrogen phosphate, disodium hydrogen phosphate, potassium dihydrogen phosphate, dipotassium hydrogen phosphate, sodium dihydrogen pyrophosphate, sodium pyrophosphate, potassium pyrophosphate, sodium chloride, potassium chloride, magnesium chloride, ammonium sulfate, sodium sulfate, sodium acetate, sodium hydrogen carbonate, and sodium carbonate. Solutions of these salts, for example, saturated aqueous solutions of these salts can be used. The kind of a solvent used for dissolving the salt is not limited to water, a single solvent or plural solvents in combination may be used, and three or more solvents may be used in combination.

As one aspect of the present invention, urea may be used instead of the salt. Extraction can be performed by allowing the use method, concentration, and the like thereof to conform to the use method of the salt. The salt and the urea may also be used in combination.

The addition of various salts to a sample promotes hydrophobic interaction. The amount of binding protein is increased to the precipitation point of the protein with increasing a salt concentration. The respective types of the salts differ in the capability of promoting the hydrophobic interaction. The different influences of the salts related to the hydrophobic interaction may be selected in consideration according to Hofmeister series. For example, a salting-out effect is also related to the hydrophobic interaction, and therefore, an increase in chaotropic effect is estimated to contribute to the decrease of them. Those skilled in the art can set each kind and condition as appropriate with reference to the solubility of a protein, and the like, and addition at a high concentration is preferred. For example, the concentration of an added salt solution or urea solution is preferably set between 0.02 and 8 mol/L, 0.2 and 8 mol/L, 0.5 and 8 mol/L, 1 and 8 mol/L, 1.5 and 8 mol/L, and 2 and 8 mol/L, and is preferably 0.1 to 8 mol/L, more preferably 0.2 to 8 mol/L, and most preferably 0.5 to 8 mol/L. For example, the concentrations of the added salt and/or urea solutions are preferably set between 0.02 and 8 mol/L, 0.2 and 8 mol/L, 0.5 and 8 mol/L, 1 and 8 mol/L, 1.5 and 8 mol/L, and 2 and 8 mol/L in terms of concentration (final concentration) in a target protein-containing sample, and more specifically, is preferably 0.02 to 8 mol/L, more preferably 0.04 to 8 mol/L is, and most preferably 0.1 to 8 mol/L. In the case of adding a salt and urea in combination, the salt and the urea of which the concentration of each is in the range described above can be used, and the salt and the urea of which the concentration in combination is in the range described above are also acceptable.

For example, in the case of using plasma as a target sample, a salt solution or a urea solution can be added in an amount 0.02 to 1 time (v/v) the amount of the sample to the sample with stirring. For example, the salt solution or the urea solution may be added in an amount 0.02 to 1 (v/v) time the amount of the sample into a test tube (test tube), followed by distilling off a solvent under nitrogen gas stream or by an evaporator, adding target plasma, and then stirring the resultant.

Deproteinization can be performed by adding such salts and/or urea at a high concentration and then adding an organic solvent. The deproteinization may use a known technology. For example, an organic solvent is added and then stirred, and a protein having a large molecular weight can be removed by centrifugation and separation with a filter for deproteinization or a column for deproteinization. The added organic solvent means an organic solvent that is completely mixed with water at room temperature, and examples thereof include methanol, ethanol, isopropanol, acetone, and acetonitrile. Methanol, ethanol, or acetonitrile is preferred. Such organic solvents may be used singly, or in mixture thereof. An organic solvent in such a case may be in mixture, and the mixture ratio thereof can be set as appropriate by those skilled in the art. For example, in the case of using the solvent mixture of methanol and acetonitrile, the mixture ratio (v/v) thereof is, for example, preferably 1:99 to 99:1, and more preferably 1:5 to 5:1, but is not limited thereto.

In order to further increase a recovery rate, water and a salt may be added to a precipitation obtained after addition of an organic solvent, and the resultant may be stirred, followed by repeatedly performing the same step plural times. In such a case, the step may be performed by setting the number of times of the performance as appropriate according to the recovery rate of a target protein.

The amount of the added water-soluble organic solvent is preferably an amount 2 or more times (v/v) and preferably 10 or less times (v/v) the amount of the sample. For example, the mixed solution of methanol and acetonitrile as the organic solvent may be added in an amount 2 or more times (v/v) of the amount of the sample with stirring.

Then, a step of separating the sample to which the salt and/or the urea, and the organic solvent have been added can be performed. For the separation of the sample, a known method can be selected and used as appropriate depending on each condition of a target protein or the like, and, for example, centrifugation operation for 5 minutes at 4° C. and 3,000 or more revolutions per minute is performed. The sample after the centrifugation is confirmed to be divided into two layers of a precipitate and a supernatant. An aliquot of the supernatant can be taken and used for subsequent measurement of the target protein. The aliquot of the supernatant can be taken using, for example, a filter for deproteinization or a column for deproteinization, and used for the subsequent measurement of the target protein.

The aliquot of the supernatant can be subjected to concentration using nitrogen gas stream or an evaporator, and concentration using a solid-phase extraction column as needed, and can be then used for measuring the target protein.

When the added salt influences subsequent analysis, a step of desalting may be performed as needed. The technique of the desalting is not particularly limited as long as the technique does not influence analysis results. For example, dialysis, ultrafiltration, gel filtration chromatography, a desalting column, a precipitation method performing precipitation and resuspension, or the like can be used, and can be selected and used as appropriate by those skilled in the art in consideration of required analysis precision or a burden such as an effort or a cost.

Depending on the property of each molecule, such as the magnitude of the molecular weight of the target protein or the stability of the molecule, a digestion step of fragmenting a peptide by various proteases (hereinafter, may be referred to as "peptide fragment") may be included, and the mixture of the obtained peptide fragment may be used for analysis. Any protease is acceptable as long as the protease allows a protein to be decomposed into a peptide fragment. As such a protease, trypsin, lysyl endopeptidase, ASP-N, and the like may be used, or may be used in combination.

For example, the obtained sample can be used in liquid chromatography (LC). HPLC (High Performance Liquid Chromatography), UHPLC (Ultra High Performance Liquid Chromatography; UHPLC) in which liquid delivery is possible at a higher pressure than in HPLC, or the like can be used for a liquid chromatography portion.

The extraction method which can be used as one aspect of the present invention is preferred because the method enables a target protein of interest to be efficiently extracted without using a surfactant and the like, and without performing a step of redissolution such as salting out, and therefore, the method has a little influence on analysis to be subsequently performed, and enables the analysis with high precision. The method is preferred because of resulting in no ionization suppression caused by a surfactant component particularly in the case of using a mass spectrometer as a detector.

The target protein extracted by the extraction method which can be used as one aspect of the present invention can be measured by a mass spectrometer, and a method other than a mass spectrometer and liquid chromatograph, for example, an analysis method using immune reaction, such as ELISA assay or latex agglutination assay, can also provide an extraction method in which contaminants can be removed to such a degree that sufficient sensitivity and specificity can be expected.

In accordance with the present invention, a step of deproteinization can be more easily performed at a higher speed, and therefore, examination for a large amount of specimen is expected to be performed in a site for clinical examination. In addition, it is possible to efficiently extract a target protein included in a biological sample, and therefore, detection sensitivity is markedly improved, whereby more accurate measurement can be performed. This is considered to be because contaminants including, for example, high molecular weight proteins can be removed.

A pretreatment kit which can be used as one aspect of the present invention comprises a salt and/or urea in the state of being mixed with a sample. Like the above-described extraction method which can be used in the present invention, the salt to be mixed with the sample also encompasses a salt solution, which may be volatile or nonvolatile. The salt and/or urea are similar to those described in the pretreatment method described above. For example, a lyophilized salt and/or urea may be included in a container such as a microtube. The salt and/or urea in the container may be a salt and/or urea in the state of being lyophilized, or may be provided in a salt solution in the state in which the salt and/or urea are dissolved in an appropriate solvent. The material of the tube is not particularly limited as long as the material does not adsorb a protein or is not influenced by an organic solvent; however, a tube made of polypropylene is preferably used. A state in which the container is enclosed is preferably maintained particularly in the case of using a volatile salt as the salt included in the container. An enclosure method is not particularly limited as long as the enclosure state is maintained.

The pretreatment kit which can be used as one aspect of the present invention may comprise a filter for deproteinization. A support included in the filter may comprise, for example, polypropylene (PP), polyvinylidene fluoride (PVDF), glass fiber (GF), polyether sulfone (PES), nylon (NY), polytetrafluoroethylene (PTFE), regenerated cellulose (RC), cellulose acetate (CA), or methacrylate butadiene styrene (MBS). A hybrid type configured by combining such plural components is also acceptable.

The pretreatment kit which can be used as one aspect of the present invention may also comprise a column for deproteinization. For example, silica, cellulose, dextran, a copolymer of styrene and divinylbenzene, a resin having the high ability of adsorbing a protein, such as octadecyl silyl (ODS), glass, ceramic, or a metal may be contained as a support included in the column. Deproteinization with the filter and deproteinization with the column may be used in combination.

Such supports may be microporous supports according to the molecular weight of a protein intended to be removed. A substance used as such a support can be selected and used as appropriate by those skilled in the art.

As the shape of the support, a shape such as a particle packing type, a monolith type, a disk shape, or a membrane shape can be selected and used as appropriate in consideration of the movement velocity and residence time of a mobile phase in the column, the concentration of a target protein during the movement, the residual binding capacity of the support, and the like by those skilled in the art.

Deproteinization can also be performed by using the above-described support for deproteinization, attached as a cartridge to a tube made of polypropylene, and passing a sample solution mixed with a salt and/or urea therethrough. Alternatively, deproteinization may also be performed by attaching a filter, housed in a container of polypropylene or the like, to a syringe, and passing a sample solution mixed with a salt and/or urea therethrough.

As means of passing the sample solution through the above-described support for deproteinization, a method with ultrafiltration using pressure is common, and means using a centrifugal device, means using a syringe type device, or the like can be selected and used as appropriate by those skilled in the art.

The pretreatment kit which can be used as one aspect of the present invention may comprise a water-soluble organic solvent. The water-soluble organic solvent is similar to that used in the pretreatment method described above. Removal of contaminants can be preferably promoted by mixing the salt and/or urea with the sample, followed by further mixing the resultant with the water-soluble organic solvent. In such a case, the salt and/or urea, and the organic solvent are preferably put in separate respective containers from the viewpoint of suppressing the nonspecific detection of contaminant substances.

The pretreatment kit which can be used as one aspect of the present invention may further contain an additive. Examples of the additive include, but are not particularly limited to, a preservative or stabilizer for stable maintenance, a reagent for forming a complex, and a separation reagent. Examples of the additive include a buffer.

In the case of using a label substance in analysis, the pretreatment kit which can be used as one aspect of the present invention may further contain a reagent required for detecting a signal based on the label substance. Those skilled in the art can select the kind of the label substance as appropriate depending on an analysis method. Examples thereof include, but are not particularly limited to, an isotope, an enzyme substrate, and a color coupler.

The pretreatment kit which can be used as one aspect of the present invention may further comprise a package insert. The package insert may comprise a description of, e.g., an operation procedure for the analysis of the target protein described above using the pretreatment kit of the present invention.

EXAMPLES

The present invention will be specifically described below with reference to Examples, which do not limit the scope of the present invention. All solid reagents used in the examples were salts, and solutions prepared by dissolving the salts in water or the like were used as salt solutions.

Example 1: Preparation of Standard Solution (1) Materials
GLP-1 (1-37) purchased from BACHEM, GLP-1 (7-36) purchased from Prospec-Tany Technogen Ltd., and GLP-1 (7-36) Amide and GLP-1 (7-37) purchased from PEPTIDE INSTITUTE, INC. were used. Moreover, HDEFERHAEGT (F) * TSDVSSYLEGQAAKEFIAWLVKGRG (hereinafter, "$^{13}C_9$, $^{15}N$-GLP-1 (1-37)"), HAEGT (F) * TSDVS-SYLEGQAAKEFIAWLVKGR (hereinafter, "$^{13}C_9$, $^{15}N$-GLP-1 (7-36)"), HAEGT (F) * TSDVSSYLEGQAAKEFI-AWLVKGR [Ami](hereinafter, "$^{13}C_9$, $^{15}N$-GLP-1(7-36) Amide"), HAEGT (F) * TSDVSSYLEGQAAKEFI-AWLVKGRG (hereinafter, "$^{13}C_9$, $^{15}N$-GLP-1 (7-37)") (manufactured by bio SYNTHESIS) were used as internal standard substances for GLP-1 (1-37), GLP-1 (7-36), GLP-1 (7-36) Amide, and GLP-1 (7-37), respectively.

(2) Preparation of Reagent
Formic acid (for precise analysis, manufactured by KANTO CHEMICAL CO., INC.), ammonium formate (special grade, manufactured by KANTO CHEMICAL CO., INC.), acetonitrile (for LC/MS, manufactured by Wako Pure Chemical Industries, Ltd.), methanol (for LC/MS, manufactured by Wako Pure Chemical Industries, Ltd.), CHAPS (manufactured by Wako Pure Chemical Industries, Ltd.), TWEEN 80 (manufactured by SIGMA) were used for preparing a reagent.

(i) Preparation of 10 mmol/L Ammonium Formate Containing 2% Formic Acid
Into 0.63 g of ammonium formate, 900 mL of Milli-Q water was added and dissolved, and 20 mL of formic acid was added to the resultant, followed by further adding Milli-Q water to achieve 1000 mL.
(ii) Preparation of Acetonitrile Containing 2% Formic Acid/100 mmol/L Ammonium Formate (9:1, v/v)
Into 0.63 g of ammonium formate, 90 mL of Milli-Q water was added and dissolved, followed by further adding Milli-Q water to achieve 100 mL. Then, 900 mL of acetonitrile was added to 100 mL of 100 mmol/L ammonium formate. Finally, 20 mL of formic acid was added to 900 mL of acetonitrile/100 mmol/L ammonium formate (9:1, v/v), followed by further adding acetonitrile/100 mmol/L ammonium formate (9:1, v/v) to achieve 1000 mL.
(iii) Preparation of 50% Acetonitrile Aqueous Solution Containing 1% Formic Acid
To 50 mL of acetonitrile, 50 mL of Milli-Q water was added, to prepare 50% acetonitrile aqueous solution. Then, 1 mL of formic acid was added to 90 mL of 50% acetonitrile aqueous solution, followed by further adding 50% acetonitrile aqueous solution to achieve 100 mL.
(iv) Preparation of 1% Formic Acid Aqueous Solution
To 90 mL of Milli-Q water, 1 mL of formic acid was added, followed by further adding Milli-Q water to achieve 100 mL.
(v) Preparation of Methanol/Acetonitrile (4:1, v/v)
To 80 mL of methanol, 20 mL of acetonitrile was added.
(vi) Preparation of Methanol/Acetonitrile (3:2, v/v)
To 60 mL of methanol, 40 mL of acetonitrile was added.
(vii) Preparation of Methanol/Acetonitrile (2:3, v/v)
To 40 mL of methanol, 60 mL of acetonitrile was added.
(viii) Preparation of Methanol/Acetonitrile (1:4, v/v)
To 20 mL of methanol, 80 mL of acetonitrile was added.
(ix) Preparation of 8 mol/L Ammonium Formate Milli-Q water was added to 0.50 g of ammonium formate to achieve 1 mL.
(x) Preparation of 5 mol/L Ammonium Formate
To 625 μL of 8 mol/L ammonium formate, 375 μL of Milli-Q water was added.
(xi) Preparation of 2 mol/L Ammonium Formate
To 400 μL of 5 mol/L ammonium formate, 600 μL of Milli-Q water was added.
(xii) Preparation of 0.5 mol/L Ammonium Formate
To 100 μL of 5 mol/L ammonium formate, 900 μL of Milli-Q water was added.
(xiii) Preparation of 1% CHAPS
Water was added to 0.01 g of CHAPS to achieve 1 mL.
(xiv) Preparation of 1% TWEEN 80
Water was added to 0.01 g of TWEEN 80 to achieve 1 mL.
(3) Preparation of Standard Solution
GLP-1 (1-37), GLP-1 (7-36), GLP-1 (7-36) Amide, GLP-1 (7-37), and the internal standard substances were dissolved in 50% acetonitrile aqueous solution containing 1% formic acid.
Into 1 mg of GLP-1 (1-37), 2.398 mL of 50% acetonitrile aqueous solution containing 1% formic acid was added, and completely dissolved to prepare a solution having a concentration of 0.1 mmol/L, which was regarded as a GLP-1 (1-37) standard solution. Into 0.05 mg of GLP-1 (7-36), 1.516 mL of 50% acetonitrile aqueous solution containing 1% formic acid was added, and completely dissolved to prepare a solution having a concentration of 0.01 mmol/L, which was regarded as a GLP-1 (7-36) standard solution. Into 0.54 mg of GLP-1 (7-36) Amide, 1.638 mL of 50% acetonitrile aqueous solution containing 1% formic acid was added, and completely dissolved to prepare a solution having a concentration of 0.1 mmol/L, which was regarded as a GLP-1 (7-36) Amide standard solution. Into 0.53 mg of GLP-1 (7-37), 1.579 mL of 50% acetonitrile aqueous solution containing 1% formic acid was added, and completely dissolved to prepare a solution having a concentration of 0.1 mmol/L, which was regarded as a GLP-1 (7-37) standard solution.

The GLP-1 (1-37), GLP-1 (7-36) Amide, and GLP-1 (7-37) standard solutions were 100-fold diluted with 50% acetonitrile aqueous solution containing 1% formic acid, and the GLP-1 (7-36) standard solution was 10-fold diluted with 50% acetonitrile aqueous solution containing 1% formic acid. The resultant solutions were regarded as mass spectrometer tuning solutions used for setting the optimum conditions of ionization and for selecting ions to be measured.

The combination of 10 μL of GLP-1 (1-37) standard solution, 100 μL of GLP-1 (7-36) standard solution, 10 μL of GLP-1 (7-36) Amide standard solution, 10 μL of GLP-1 (7-37) standard solution, and 870 μL of 50% acetonitrile aqueous solution containing 1% formic acid was performed to prepare 1 μmol/L of mixed standard solution for confirming a recovery rate.

Example 2: Determination of Mass Spectrometry Conditions

A connector of FIG. 1 was switched from a two-way type to a three-way type, and a mass spectrometer tuning solution was introduced into an ion source using a syringe pump. In such a case, a mobile phase mixed using an HPLC pump (LC-20A, manufactured by SHIMADZU CORPORATION) was introduced with the tuning solution into the ion source.

While confirming a precursor ion (parent ion) to be used in quantification, the spray position of the ion source (ESI, Turbo V Spray, AB SCIEX) of a mass spectrometer (QTRAP 5500, AB SCIEX) was adjusted so that the highest ionic strength thereof was achieved.

After the completion of the adjustment of the spray position, a declustering potential (orifice voltage; DP), an ion attraction voltage (EP), a high applied voltage (ionspray voltage; IS), the gas pressures of GS1 and GS2 (GS1 and GS2), and a temperature (TEM) were adjusted.

Then, a product ion (daughter ion) was searched from the precursor ion (parent ion), and a collision gas amount (CAD), an energy voltage involved in collision cleavage (CE), and the voltage of a collision cell outlet (CXP) were adjusted so that the highest ionic strength thereof was achieved.

The mass spectrometry conditions determined by the methods described above are set forth in Tables 1 and 2. A common ionization condition is set forth in Table 1. The mass spectrometry conditions (MS/MS conditions) of each component are set forth in Table 2.

TABLE 1

Ionization Conditions

| Ion source | Ionization mode Positive ESI (Turbo V-spray) | | | |
|---|---|---|---|---|
| | IS | GS1 | GS2 | TEM |
| | 3000 V | 40 psi Dry air | 70 psi Dry air | 600° C. |

TABLE 2

Mass Spectrometry Conditions (MS/MS Conditions)

| T/A | Q1 | Q3 | DP | EP | CE | CXP |
|---|---|---|---|---|---|---|
| GLP-1 (1-37) | 695.9 | 771.1 | 46 | 10 | 24 | 9.5 |
| GLP-1 (1-37)_I.Std | 697.6 | 771.1 | 46 | 10 | 24 | 9.5 |
| GLP-1 (7-36) | 660.9 | 752.3 | 60 | 10 | 24 | 9.2 |
| GLP-1 (7-36)_I.Std | 663.6 | 752.9 | 60 | 10 | 24 | 9.2 |
| GLP-1 (7-36) Amide | 660.3 | 751.6 | 70 | 10 | 24 | 9.2 |
| GLP-1 (7-36) Amide_I.Std | 663.2 | 752.4 | 70 | 10 | 24 | 9.2 |
| GLP-1 (7-37) | 672.1 | 771.1 | 41 | 10 | 24 | 9.5 |
| GLP-1 (7-37)_I.Std | 674.1 | 771.2 | 41 | 10 | 24 | 9.5 |

Example 3: Setting of HPLC Conditions

HPLC conditions at which GLP-1 (1-37), GLP-1 (7-36), GLP-1 (7-36) Amide, and GLP-1 (7-37) can be separated were examined using the mixed standard solution for confirming a recovery rate, produced in Example 1.

A Nexera MP system (manufactured by SHIMADZU CORPORATION) was used as an HPLC device, and a Cadenza CD-C18 column (particle diameter of 3 μm, inner diameter of 2.0 mm×length of 150 mm; manufactured by Imtakt) was used as an HPLC column.

Linear gradient conditions in which 10 mmol/L ammonium formate containing 2% formic acid was used as the aqueous mobile phase of a separation solution, and acetonitrile containing 2% formic acid/100 mmol/L ammonium formate (9:1, v/v) was used as an organic mixture mobile phase were set. A flow rate was set at 0.6 mL/min. An example of the gradient conditions is set forth in Table 3.

TABLE 3

Gradient Conditions (Linear Gradient)

| Time (min) | Mobile Phase B(%) |
|---|---|
| 0.00 | 32 |
| 0.50 | 32 |
| 5.00 | 38 |
| 6.50 | 38 |
| 6.51 | 90 |
| 8.00 | 90 |
| 8.01 | 32 |
| 10.00 | 32 |

Example 4: Evaluation of Extraction Method

A deproteinization method by addition of an organic solvent was used as a pretreatment method of extracting GLP-1 (1-37), GLP-1 (7-36), GLP-1 (7-36) Amide, and GLP-1 (7-37) from a biological sample. Water, ammonium formate, or a surfactant (comparative example) was added to the biological sample prior to the deproteinization, methanol or a liquid mixture of methanol and acetonitrile was added as the organic solvent, and the recovery rate of each component was confirmed.

A sample obtained after transferring 2 mL of Human 2Na-EDTA plasma, pool of donors (BIOPREDIC) as the biological sample into Nipro Neotube (2 mL, DPP inhibitor+EDTA-2Na, manufactured by NIPRO CORPORATION) and mixing the biological sample by inversion was used.

For the sample for confirming a recovery rate, 5 μL of mixed standard solution for confirming a recovery rate (1 μmol/L each) was added to 50 μL of the above-described plasma, and stirred for 1 minute, followed by adding 10 μL of additive 1 described below. The resultant was stirred for 1 minute, 150 μL of organic solvent 1 described below was added to the resultant, and stirred for 1 minute, followed by performing centrifugation (CF16RXII, Hitachi Koki) set at 4° C. for 5 minutes at 4,000 revolutions per minute. A 10 μL aliquot of the supernatant thereof was taken, 10 μL of internal standard substance (0.5 μmol/L each), 40 μL of 50% acetonitrile aqueous solution containing 1% formic acid, and 40 μL of 1% formic acid aqueous solution were added to the aliquot, and the resultant was mixed to make the sample for confirming a recovery rate.

Water, 0.5 mol/L ammonium formate, 2 mol/L ammonium formate, 5 mol/L ammonium formate, 8 mol/L ammonium formate, 1% CHAPS, or 1% TWEEN 80 was used as the additive 1. Methanol, methanol/acetonitrile (4:1, v/v), methanol/acetonitrile (3:2, v/v), methanol/acetonitrile (2:3, v/v), or methanol/acetonitrile (1:4, v/v) was used as the organic solvent 1.

For a reference sample for confirming a recovery rate, 5 μL of 50% acetonitrile aqueous solution containing 1% formic acid was added to 50 μL of the plasma described above, and stirred for 1 minute, followed by adding 10 μL of the additive 1. The resultant was stirred for 1 minute, 150 μL of the organic solvent 1 was then added thereto, and stirred for 1 minute, followed by performing centrifugation (CF16RXII, Hitachi Koki) set at 4° C. for 5 minutes at 4,000 revolutions per minute. A 10 μL aliquot of the supernatant thereof was taken, 10 μL of internal standard substance (0.5 μmol/L each), 10 μL of STD solution 1 described later, 30 μL of 50% acetonitrile aqueous solution containing 1% formic acid, and 40 μL of 1% formic acid aqueous solution were added to the aliquot, and the resultant was mixed to make the reference sample for confirming a recovery rate.

The STD solution 1, obtained by adding 5 μL of mixed standard solution for confirming a recovery rate (1 μmol/L each), 10 μL of water, and 150 μL of the organic solvent 1 to 50 μL of 1% formic acid aqueous solution, and mixing the resultant, was used.

The sample for confirming a recovery rate and the reference sample for confirming a recovery rate were measured under the conditions of Examples 2 and 3, and the peak area ratio of each component (peak area value of standard substance/peak area value of internal standard substance) was calculated using software, Analyst 1.6.2 (AB SCIEX), attached to a mass spectrometer. A recovery rate (%) was determined from the following Equation.

Recovery rate (%)=peak area ratio of sample for confirming recovery rate/peak area ratio of reference sample for confirming recovery rate×100

The evaluation results of the extraction method are set forth in Tables 4 to 7. For each added organic solvent, a solvent having a higher recovery rate than that in the case of using water, 1% CHAPS, and TWEEN 80 as the additives was indicated as bold text.

TABLE 4

Comparison Results of Recovery Rates (%) of GLP-1 (1-37) between Extraction Method of the Present Invention and Existing Method

| | Added Organic Solvent | | | | |
| Additive | Methanol | Methanol/ Acetonitrile (4:1) | Methanol/ Acetonitrile (3:2) | Methanol/ Acetonitrile (2:3) | Methanol/ Acetonitrile (1:4) |
| --- | --- | --- | --- | --- | --- |
| None (Water) | 7.1 | 6.7 | 5.2 | 5.8 | 2.3 |
| 0.5 mol/L Ammonium Formate | 9.3 | 10.7 | 15.9 | 12.9 | 10.8 |
| 2 mol/L Ammonium Formate | 16.4 | 15.4 | 15.6 | 14.0 | 8.9 |
| 5 mol/L Ammonium Formate | 19.2 | 26.6 | 22.7 | 24.0 | 14.3 |
| 8 mol/L Ammonium Formate | 19.4 | 25.7 | 36.4 | 30.6 | 17.2 |
| 1% CHAPS | 9.7 | 12.1 | 12.2 | 15.0 | 5.7 |
| 1% TWEEN 80 | 9.5 | 11.7 | 15.4 | 13.9 | 5.6 |

TABLE 5

Comparison Results of Recovery Rates (%) of GLP-1 (7-36) between Extraction Method of the Present Invention and Existing Method

| | Added Organic Solvent | | | | |
| Additive | Methanol | Methanol/ Acetonitrile (4:1) | Methanol/ Acetonitrile (3:2) | Methanol/ Acetonitrile (2:3) | Methanol/ Acetonitrile (1:4) |
| --- | --- | --- | --- | --- | --- |
| None (Water) | 35.9 | 46.1 | 29.4 | 30.1 | 18.2 |
| 0.5 mol/L Ammonium Formate | 55.5 | 51.4 | 58.0 | 55.2 | 53.7 |
| 2 mol/L Ammonium Formate | 42.3 | 62.0 | 54.5 | 58.9 | 61.7 |
| 5 mol/L Ammonium Formate | 71.0 | 77.4 | 69.4 | 67.1 | 49.9 |
| 8 mol/L Ammonium Formate | 72.8 | 62.6 | 77.7 | 61.1 | 72.2 |
| 1% CHAPS | 56.9 | 67.5 | 68.7 | 44.7 | 34.8 |
| 1% TWEEN 80 | 47.8 | 72.0 | 57.2 | 63.1 | 29.2 |

TABLE 6

Comparison Results of Recovery Rates (%) of GLP-1 (7-36) Amide between Extraction Method of the Present Invention and Existing Method

| | Added Organic Solvent | | | | |
| Additive | Methanol | Methanol/ Acetonitrile (4:1) | Methanol/ Acetonitrile (3:2) | Methanol/ Acetonitrile (2:3) | Methanol/ Acetonitrile (1:4) |
| --- | --- | --- | --- | --- | --- |
| None (Water) | 51.1 | 62.1 | 67.2 | 69.0 | 44.7 |
| 0.5 mol/L Ammonium Formate | 56.6 | 74.5 | 92.9 | 66.5 | 60.3 |

TABLE 6-continued

Comparison Results of Recovery Rates (%) of
GLP-1 (7-36) Amide between Extraction Method
of the Present Invention and Existing Method

| Additive | Methanol | Methanol/Acetonitrile (4:1) | Methanol/Acetonitrile (3:2) | Methanol/Acetonitrile (2:3) | Methanol/Acetonitrile (1:4) |
|---|---|---|---|---|---|
| | | Added Organic Solvent | | | |
| 2 mol/L Ammonium Formate | 90.4 | 82.6 | 84.1 | 89.1 | 88.6 |
| 5 mol/L Ammonium Formate | 82.9 | 94.7 | 85.5 | 88.9 | 87.8 |
| 8 mol/L Ammonium Formate | 87.6 | 98.4 | 99.7 | 101.4 | 89.0 |
| 1% CHAPS | 63.6 | 62.3 | 74.2 | 78.6 | 64.3 |
| 1% TWEEN 80 | 53.4 | 73.0 | 86.3 | 74.1 | 82.0 |

TABLE 7

Comparison Results of Recovery Rates (%) of GLP-I (7-37) between
Extraction Method of the Present Invention and Existing Method

| Additive | Methanol | Methanol/Acetonitrile (4:1) | Methanol/Acetonitrile (3:2) | Methanol/Acetonitrile (2:3) | Methanol/Acetonitrile (1:4) |
|---|---|---|---|---|---|
| | | Added Organic Solvent | | | |
| None (Water) | 46.8 | 57.8 | 48.3 | 36.5 | 29.5 |
| 0.5 mol/L Ammonium Formate | 64.7 | 64.9 | 79.1 | 57.3 | 47.4 |
| 2 mol/L Ammonium Formate | 50.0 | 67.5 | 63.8 | 59.4 | 66.1 |
| 5 mol/L Ammonium Formate | 70.8 | 76.8 | 73.5 | 79.0 | 57.0 |
| 8 mol/L Ammonium Formate | 71.1 | 72.4 | 98.1 | 76.3 | 73.8 |
| 1% CHAPS | 49.9 | 61.1 | 64.9 | 53.7 | 37.0 |
| 1% TWEEN 80 | 55.8 | 62.3 | 62.9 | 64.4 | 38.7 |

The examination results revealed that the deproteinization with the addition of the organic solvent after the addition of ammonium formate to the biological sample resulted in a recovery rate (%) equivalent to or greater than that in the existing method.

Example 5: Preparation of Standard Solution (1) Material

"FNDC5 (47-72)" having 47th to 72nd sequences of Fibronectin type III domain-containing protein 5 (FNDC5) (amino acid sequence: ANSAVVSWDVLEDEV-VIGFAISQQKK), purchased from Scrum Inc., was used. ANSAVVSWDVLEDEVVIGFAISQQK (K) *, hereinafter "$^{13}C_6$, $^{15}N_2$-FNDC5 (47-72)" (manufactured by Scrum Inc.), was used as an internal standard substance for FNDC5 (47-72).

(2) Preparation of Reagents

In addition to the reagents prepared in Example 1, the following reagents were prepared. Ammonium acetate, ammonium hydrogen carbonate, potassium dihydrogen phosphate, and salt (special grade, manufactured by KANTO CHEMICAL CO., INC.) were used for the preparation of the reagents.

(i) Preparation of 0.1% Formic Acid Aqueous Solution

Milli-Q water was added to 1 mL of formic acid to achieve 1000 mL.

(ii) Preparation of Acetonitrile Containing 0.1% Formic Acid

Acetonitrile was added to 1 mL of formic acid to achieve 1000 mL.

(iii) Preparation of Methanol/Acetonitrile (1:1, v/v)

To 50 mL of methanol, 50 mL of acetonitrile was added.

(iv) Preparation of 8 mol/L Ammonium Formate

Milli-Q water was added to 0.62 g of ammonium formate to achieve 1 mL.

(v) Preparation of Saturated Ammonium Hydrogen Carbonate

Ammonium hydrogen carbonate was added to 10 mL of Milli-Q water, and the resultant was saturated.

(vi) Preparation of Saturated Potassium Dihydrogen Phosphate

Potassium dihydrogen phosphate was added to 10 mL of Milli-Q water, and the resultant was saturated.

(vii) Preparation of Saturated Solution of Salt

A salt was added to 10 mL of Milli-Q water, and the resultant was saturated.

(viii) Preparation of Saturated Sodium Carbonate

Sodium carbonate was added to 10 mL of Milli-Q water, and the resultant was saturated.

(3) Preparation of Standard Solution

FNDC5 (47-72) and the internal standard substance were dissolved in DMSO (special grade, manufactured by Wako Pure Chemical Industries, Ltd.).

To 1 mg of FNDC5 (47-72), 1 mL of DMSO was added, and completely dissolved to prepare a solution having a concentration of 1 mg/mL, which was regarded as an FNDC5 (47-72) standard solution.

The FNDC5 (47-72) standard solution was 500-fold diluted with 50% acetonitrile aqueous solution containing 1% formic acid. The resultant solution was regarded as a mass spectrometer tuning solution used for setting the optimum conditions of ionization and for selecting ions to be measured.

The combination of 10 μL of FNDC5 (47-72) standard solution and 990 μL of 50% acetonitrile aqueous solution containing 1% formic acid was performed to prepare 10 μg/mL of standard solution for confirming a recovery rate.

Example 6: Determination of Mass Spectrometry Conditions

Mass spectrometry conditions were set by a method similar to that of Example 2. The determined mass spectrometry conditions are set forth in Tables 8 and 9. A common ionization condition is set forth in Table 8. The mass spectrometry conditions (MS/MS conditions) of each component are set forth in Table 9.

TABLE 8

Ionization Conditions

Ionization mode
Positive ESI (Turbo V-spray)

| Ion source | IS | GS1 | GS2 | TEM |
|---|---|---|---|---|
| | 3000 V | 40 psi Dry air | 60 psi Dry air | 650° C. |

TABLE 9

Mass Spectrometry Conditions (MS/MS Conditions)

| T/A | Q1 | Q3 | DP | EP | CE | CXP |
|---|---|---|---|---|---|---|
| FNDC5 (47-72) | 945.3 | 1196.2 | 55 | 10 | 38 | 14.7 |
| FNDC5 (47-72)_I.Std | 947.9 | 1200.0 | 55 | 10 | 38 | 14.7 |

Example 7: Setting of HPLC Conditions

HPLC conditions at which FNDC5 (47-72) can be analyzed were examined using the standard solution for confirming a recovery rate, produced in Example 5.

A Nexera MP system (manufactured by SHIMADZU CORPORATION) was used as an HPLC device, and an XBridge peptide BEH C18 column (300 Å, particle diameter of 3.5 m, inner diameter of 2.1 mm×length of 50 mm; manufactured by Waters) was used as an HPLC column.

Linear gradient conditions in which 0.1% formic acid aqueous solution was used as the aqueous mobile phase of a separation solution, and acetonitrile containing 0.1% formic acid was used as an organic mixture mobile phase were set. A flow rate was set at 0.5 mL/min. An example of the gradient conditions is set forth in Table 10.

TABLE 10

Gradient Conditions (Linear Gradient)

| Time (min) | Mobile Phase B(%) |
|---|---|
| 0.00 | 5 |
| 5.00 | 40 |
| 6.00 | 40 |
| 6.01 | 90 |
| 7.00 | 90 |
| 7.01 | 5 |
| 9.00 | 5 |

Example 8: Evaluation of Extraction Method

A deproteinization method by addition of methanol/acetonitrile (1:1, v/v) as an organic solvent was used as a pretreatment method of extracting FNDC5 (47-72) from a biological sample. Water, ammonium formate, ammonium acetate, ammonium hydrogen carbonate, sodium carbonate, a surfactant (comparative example), potassium dihydrogen phosphate or a salt was added to the biological sample prior to the deproteinization, and the recovery rate of FNDC5 (47-72) was confirmed.

Like Example 3, Human 2Na-EDTA plasma, pool of donors (BIOPREDIC) was used as the biological sample.

For the sample for confirming a recovery rate, 2.5 μL of standard solution for confirming a recovery rate (10 μg/mL each) was added to 25 μL of the above-described plasma, and stirred for 1 minute, followed by adding 5 μL of additive 2 described below. The resultant was stirred for 1 minute, 75 μL of methanol/acetonitrile (1:1, v/v) was added to the resultant, and stirred for 1 minute, followed by performing centrifugation (CF16RXII, Hitachi Koki) set at 4° C. for 5 minutes at 4,000 revolutions per minute. A 25 μL aliquot of the supernatant thereof was taken, 2.5 μL of internal standard substance (10 μg/mL) and 25 μL of 50% acetonitrile aqueous solution containing 1% formic acid were added to the aliquot, and the resultant was mixed to make the sample for confirming a recovery rate.

Water, 8 mol/L ammonium formate, 8 mol/L ammonium acetate, saturated ammonium hydrogen carbonate, saturated sodium carbonate, 1% CHAPS, 1% TWEEN 80, saturated potassium dihydrogen phosphate, or a saturated solution of a salt was used as the additive 2.

For a reference sample for confirming a recovery rate, 2.5 μL of 50% acetonitrile aqueous solution containing 1% formic acid was added to 25 μL of the plasma described above, and stirred for 1 minute, followed by adding 5 μL of the additive 2. The resultant was stirred for 1 minute, 75 μL of methanol/acetonitrile (1:1, v/v) was then added thereto, and stirred for 1 minute, followed by performing centrifugation (CF16RXII, Hitachi Koki) set at 4° C. for 5 minutes at 4,000 revolutions per minute. A 25 μL aliquot of the supernatant thereof was taken, 2.5 μL of internal standard substance (10 μg/mL) and 25 μL of STD solution 2 were added to the aliquot, and the resultant was mixed to make the reference sample for confirming a recovery rate.

The STD solution 2, obtained by adding 50 μL of standard solution for confirming a recovery rate (10 μg/mL) to 1025 μL of 50% acetonitrile aqueous solution containing 1% formic acid, and mixing the resultant, was used.

The sample for confirming a recovery rate and the reference sample for confirming a recovery rate were measured under the conditions of Examples 6 and 7, and the peak area ratio of FNDC5 (47-72) (peak area value of standard substance/peak area value of internal standard substance) was calculated using software, Analyst 1.6.2 (AB SCIEX), attached to a mass spectrometer. A recovery rate (%) was determined from the following Equation.

Recovery rate (%)=peak area ratio of sample for confirming recovery rate/peak area ratio of reference sample for confirming recovery rate×100

The evaluation results of the extraction method are set forth in Table 11. A solvent having a higher recovery rate than that in the case of using water, 1% CHAPS, and TWEEN 80 as the additives was indicated as bold text.

TABLE 11

Comparison Results of Recovery Rates (%) of FNDC5 (47-72) between Extraction Method of the Present Invention and Existing Method (Extracting Solvent: Methanol/Acetonitrile (1:1, v/v))

| Additive | Recovery Rate (%) |
|---|---|
| None (Water) | 10.4 |
| 8 mol/L Ammonium Formate | 19.9 |
| 8 mol/L Ammonium Acetate | 29.1 |
| Saturated Ammonium Hydrogen Carbonate | 53.5 |
| Saturated Sodium Carbonate | 74.1 |

TABLE 11-continued

Comparison Results of Recovery Rates (%) of FNDC5 (47-72) between Extraction Method of the Present Invention and Existing Method (Extracting Solvent: Methanol/Acetonitrile (1:1, v/v))

| Additive | Recovery Rate (%) |
| --- | --- |
| 1% CHAPS | 11.0 |
| 1% TWEEN 80 | 11.1 |
| Saturated Potassium Dihydrogen Phosphate | 10.4 |
| Saturated Solution of Salt | 20.3 |

The above results showed that the addition and mixture of an organic solvent after the addition of a salt at a high concentration to a sample result in removal of a protein included in a sample, and in drastic improvement in the recovery rate of a target protein. Use of the present invention enabled accurate and high-speed handling of a slight amount of target protein and a large amount of specimen. This is presumed to be because a contaminant high-molecular-weight protein was able to be efficiently removed without involving the target protein. It was suggested that the use is particularly effective in the case of occurrence of a phenomenon that a high-molecular-weight protein and a target protein coprecipitate.

INDUSTRIAL APPLICABILITY

The extraction method of the present invention is preferred because the method enables a target protein of interest to be efficiently extracted without using a surfactant, and therefore, the method has a little influence on analysis to be subsequently performed, and enables the analysis with high precision. The method is preferred because of resulting in no ionization suppression caused by a surfactant component particularly in the case of using a mass spectrometer as a detector.

In accordance with the present invention, a step of deproteinization can be more easily performed at a higher speed, and therefore, examination for a large amount of specimen is expected to be performed in a site for clinical examination. In addition, it is possible to remove contaminants including a protein contained in a biological sample, and therefore, detection sensitivity is markedly improved, whereby more accurate analysis can be performed.

What is claimed is:

1. A method of extracting one or more target protein(s) from a sample derived from a living body by a deproteinization method, comprising:
    extracting said one or more target protein(s) by using a salt at a concentration of 0.02 to 8 mol/L, and a water-soluble organic solvent, wherein
    said extracting comprises:
    adding the salt at a concentration of 0.02 to 8 mol/L to the sample derived from the living body with stirring:
    adding the water-soluble organic solvent to the sample to which the salt have been added, wherein an amount of the added water-soluble organic solvent is twice or more (v/v) an amount of the sample derived from the living body;
    separating the sample to which the water-soluble organic solvent has been added; and
    collecting a supernatant comprising said one or more target protein(s) after the separation,
    wherein the sample is selected from the group consisting of blood, plasma, serum, urine, stool, saliva, sputum, sperm; secretion, excreta, or swab from vagina, nose, rectum, urethra, or pharynx; secretory fluid from lacrimal duct, bronchoalveolar lavage fluid (BALF), pleural effusion, and a biopsy tissue sample,
    wherein said one or more target protein(s) is a protein being able to be dissolved in a water-soluble organic solvent, and wherein said one or more target protein(s) has a molecular weight of 50,000 Da or less.

2. The method according to claim 1, wherein the water-soluble organic solvent is one or more selected from methanol, ethanol, isopropanol, acetone, and acetonitrile.

3. The method according to claim 1, wherein the salt is an ammonium salt, a sodium salt, a potassium salt, a magnesium salt, or a solution of each of the salts.

4. The method according to claim 1, wherein the salt is one or more salts selected from ammonium formate, ammonium carbonate, ammonium hydrogen carbonate, ammonium acetate, ammonium dihydrogen phosphate, diammonium hydrogen phosphate, sodium dihydrogen phosphate, disodium hydrogen phosphate, potassium dihydrogen phosphate, dipotassium hydrogen phosphate, sodium dihydrogen pyrophosphate, sodium pyrophosphate, potassium pyrophosphate, sodium chloride, potassium chloride, magnesium chloride, ammonium sulfate, sodium sulfate, sodium acetate, sodium hydrogen carbonate, and sodium carbonate.

5. The method according to claim 1, wherein said one or more target protein(s) is one or more selected from a group consisting of glucagon or an analog thereof, glucagon-like peptide-1 (GLP-1) or an analog thereof, glucose-dependent insulinotropic polypeptide (GIP) or an analog thereof, an incretin other than the above or an analog thereof, partial peptides (K1 to K20) of keratin (cytokeratin) or analogs thereof, dynorphin or an analog thereof, GRF or an analog thereof, insulin or an analog thereof, an HIV virus-derived peptide or an analog thereof, an SR protein family member or an analog thereof, peptide YY (PYY) or an analog thereof, adrenocorticotrophic hormone (ACTH) or an analog thereof, corticotropin-releasing hormone (CRH) or an analog thereof, corticotropin-like intermediate-lobe peptide (CLIP) or an analog thereof, melanocyte-stimulating hormone (MSH) or an analog thereof, lipotropin (LPH) or an analog thereof, amyloid β (Aβ) or an analog thereof, growth hormone (GH) or an analog thereof, a growth hormone-releasing factor (GRF or GHRF) or an analog thereof, growth factors or growth stimulators, or analogs thereof, a VGF-derived peptide or an analog thereof, isoleucyl-seryl-bradykinin or an analog thereof, a natriuretic peptide or an analog thereof, a natriuretic factor or an analog thereof, a precursor of a natriuretic peptide, or an analog thereof, midkine (MK) or an analog thereof, a neuromedin or an analog thereof, gastrin or an analog thereof, gastrin-releasing peptide or an analog thereof, endorphin (EP) or an analog thereof, neoendorphin or an analog thereof, proopiomelanocortin (POMC) or an analog thereof, enkephalin (PENK) or an analog thereof, dynorphin or an analog thereof, adrenorphin or an analog thereof, amidorphin or an analog thereof, opiorphin or an analog thereof, casomorphin or an analog thereof, gluten exorphin or an analog thereof, gliadorphin or an analog thereof, rubiscolin or an analog thereof, deltorphin or an analog thereof, an opioid peptide such as dermorphin, or an analog thereof, adrenomedullin (AM) or an analog thereof, a neuropeptide such as neuropeptide 1, neuropeptide 2, neuropeptide AF, neuropeptide B, neuropeptide FF, neuropeptide G, neuropeptide K, neuropeptide S, neuropeptide SF, neuropeptide W, neuropeptide Y, neuropeptide Y C-terminal flanking peptide, neuropeptide γ, neuropeptide NEI, or neuropeptide NGE, or an analog thereof, nociceptin (orphanin FQ) or an analog thereof, an oxytocin or an analog thereof, urocortin or an analog thereof, interferon-γ or an analog thereof, rat neutrophil chemotactic factor-1 (CINC-1/gro) or an analog thereof, parathyroid hormone (PTH) or an analog thereof, ovalbumin (OVA) or an analog thereof, angiotensinogen, angiotensins I to IV or analogs thereof, irisin or an analog thereof, substance P or an analog thereof, neurokinin A or an analog thereof, neurokinin B or an analog thereof, copeptin or an analog thereof, ghrelin or an analog thereof, motilin or an analog thereof, erythropoietin or an analog thereof, endothelin or an analog thereof, luteinizing hormone or an analog thereof, orexin or an analog thereof, pituitary adenylate cyclase-activating peptide or an analog thereof, calcitonin or an analog thereof, calcitonin gene-related peptide or an analog thereof, katacalcin or an analog thereof, vasoactive intestinal peptide or an analog thereof, thyrotropin-releasing hormone (TRH) or an analog thereof, cholecystokinin or an analog thereof, plant peptide hormone or an analog thereof, gonadotrophic hormone or an analog thereof, secretin or an analog thereof, somatostatin or an analog thereof, pregnant mare serum gonadotropin or an analog thereof, vasopressin (VP) or an analog thereof, vasotocin or an analog thereof, parathormone (PTH) or an analog thereof, bombesin or an analog thereof, follicle-stimulating hormone or an analog thereof, leuprorelin or an analog thereof, relaxin or an analog thereof, liraglutide or an analog thereof, leptin or an analog thereof, peptide B or an analog thereof, peptide E or an analog thereof, peptide F or an analog thereof, BAMP22P or an analog thereof, morphine or an analog thereof, neurophysin 1 or an analog thereof, neurophysin 2 or an analog thereof, anthorine or an analog thereof, cortistatin or an analog thereof, RF amide-related peptide or an analog thereof, pancreatic polypeptide Y or an analog thereof, pancreatic polypeptide YY (PP) or an analog thereof, islet amyloid polypeptide or an analog thereof, amylin or an analog thereof, intermedin or an analog thereof, ranatensin or an analog thereof, glicentin or an analog thereof, oxyntomodulin or an analog thereof, vasoactive intestinal peptide (VIP) or an analog thereof, pituitary adenylate cyclase activating polypeptide (PACPA) or an analog thereof, somatoliberin or an analog thereof, somatorelin or an analog thereof, sermorelin or an analog thereof, urotensin or an analog thereof, kininogen or an analog thereof, kallidin or an analog thereof, kinin or an analog thereof, neurotensin or an analog thereof, chromogranin or an analog thereof, granin or an analog thereof, vasostatin or analogs thereof, secretogranin or an analog thereof, CCB or an analog thereof, GAWK or an analog thereof, EM66 or an analog thereof, obestatin or an analog thereof, galanin or an analog thereof, galanin message-associated peptide or an analog thereof, galanin-like peptide or an analog thereof, gonadotrophic hormone-releasing hormone (GnRH) or an analog thereof, gonadoliberin or an analog thereof, neurexophilins (NXPHs) 1 to 4 or analogs thereof, parathormone-like hormone (PTHLH) or an analog thereof, osteostatin or an analog thereof, melanin-concentrating hormone (MCH) or an analog thereof, hypocretin or an analog thereof, cocaine- and amphetamine-regulated transcript (CART) or an analog thereof, agouti-related peptide (AGRP) or an analog thereof, prolactin or an analog thereof, prolactin-releasing peptide (PrRP) or an analog thereof, apelin or an analog thereof, kisspeptin or an analog thereof, metastin or an analog thereof, diazepam binding inhibitor or an analog thereof, cerberin (CBLN) or an analog thereof, obesin or an analog thereof, adiponectin or an analog thereof, visfatin or an analog thereof, PBEF or an analog thereof, resistin or an analog thereof, an adipose tissue-specific secretory factor or an analog thereof, or a hypoxia-induced mitogenic factor or an analog thereof, colon/intestine-specific cysteine-rich protein or an analog thereof, colon cancer-specific gene product or an analog thereof, secretory DNA/calcium-binding protein nuclebindin or an analog thereof, nesfatin or an analog thereof, and precursors of the peptides described above.

6. The method according to claim 1, wherein the sample is blood, plasma, or serum.

7. A method of analyzing one or more target protein(s), comprising collecting a supernatant containing one or more target protein(s) by the method according to claim 1, and analyzing said one or more target protein(s) using the supernatant.

8. The method according to claim 7, wherein said one or more target protein(s) is analyzed by a UV detector, a fluorescence detector, or a mass spectrometer.

9. The method according to claim 1, wherein said one or more target protein(s) has a molecular weight of 25,000 Da or less.

10. The method according to claim 1, wherein said one or more target protein(s) has a molecular weight of 12,000 Da or less.

* * * * *